United States Patent
Lambrecht et al.

(10) Patent No.: US 6,720,456 B2
(45) Date of Patent: Apr. 13, 2004

(54) PROCESS FOR THE PREPARATION OF 2,3-PENTANEDIONE

(75) Inventors: Stefan Lambrecht, Holzminden (DE); Oliver Franke, Höxter (DE); Klaus Zahlmann, Holzminden (DE)

(73) Assignee: Symrise GmbH & Co. KG (DE)

( * ) Notice: Subject to any disclaimer, the term of this patent is extended or adjusted under 35 U.S.C. 154(b) by 0 days.

(21) Appl. No.: 10/289,546

(22) Filed: Nov. 7, 2002

(65) Prior Publication Data

US 2003/0092942 A1 May 15, 2003

(30) Foreign Application Priority Data

Nov. 12, 2001 (DE) .......................... 101 55 553

(51) Int. Cl.[7] .............................. C07C 45/00
(52) U.S. Cl. ................. 568/391; 568/402; 568/404; 568/412
(58) Field of Search ................ 568/391, 402, 568/404, 412

(56) References Cited

U.S. PATENT DOCUMENTS

| 2,799,707 A | 7/1957 | Dermer ................... 260/590 |
| 6,242,653 B1 | 6/2001 | Aquila et al. |

FOREIGN PATENT DOCUMENTS

| EP | 0 983 987 A1 | 3/2000 | ........... C07C/45/29 |

OTHER PUBLICATIONS

DataBase Crossfire Beilstein Online! Beilstein Institut zur Foerderung der Chemischen WissenSchaften, Franfurt am Main, DE; Database Accession No. 643575, XP002230743 & Neuberg et al.: Biochem. Z. vol. 275, p. 342.

*Primary Examiner*—Johann Richter
*Assistant Examiner*—Sikarl A. Witherspoon
(74) *Attorney, Agent, or Firm*—Pendorf & Cutliff

(57) ABSTRACT

The present invention relates to a novel process for the preparation of 2,3-pentanedione starting with hydroxyacetone and paraldehyde.

6 Claims, No Drawings

PROCESS FOR THE PREPARATION OF 2,3-PENTANEDIONE

FIELD OF THE INVENTION

The present invention relates to a novel process for the preparation of 2,3-pentanedione, wherein the process is derived from hydroxyacetone and paraldehyde.

BACKGROUND OF THE INVENTION 2,3-Pentanedione is an important aroma substance (Allured's Flavor and Fragrance Materials—1995, Allured Publishing Corporation, 1995, p. 22). In addition, 2,3-pentanedione is an important raw material for the preparation of alkyl-substituted pyrazines (DE 100 22 361 C1).

The preparation of 2,3-pentanedione is known per se. The preparation takes place, for example, starting with hydroxyacetone and paraldehyde in a single-stage process and can be illustrated by the following scheme:

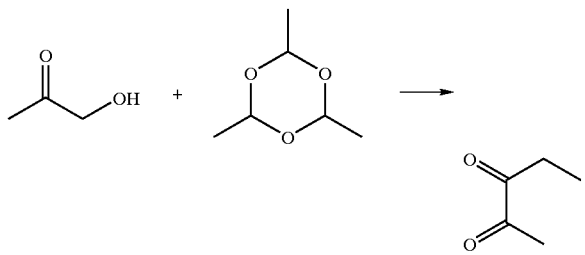

The known synthesis process, as disclosed in U.S. Pat. No. 2,799,707 produces the desired 2,3-pentanedione from hydroxyacetone and paraldehyde in an uneconomic process. The poor yield of 48% of 2,3-pentanedione and the long reaction time (about 60 hours) are particularly disadvantageous.

A process, which produces 2,3-pentanedione in a simple manner and in good yield, is therefore of great interest.

SUMMARY OF THE INVENTION

The present invention therefore provides a process for the preparation of 2,3-pentanedione from hydroxyacetone and paraldehyde, wherein the reaction is carried out in the presence of an aqueous phase containing a strong organic or inorganic acid with a pKa value of less than or equal to 4 and in the presence of a phase transfer catalyst.

DETAILED DESCRIPTION OF THE INVENTION

It has been found that the addition of a phase transfer catalyst can improve the yield compared with the prior art (See for example, U.S. Pat. No. 2,799,707). In addition, the reaction time can be shortened and the space-time yield increased.

Preference is given to the addition of a metering mixture containing hydroxyacetone and paraldehyde and optionally a diluent to an aqueous solution containing an acid with a pKa value of less than or equal to 4 and a phase transfer catalyst.

Suitable phase transfer catalysts for the process according to the present invention include, for example, phosphonium, sulfonium and ammonium compounds. Preference is given to ammonium compounds. Preferred ammonium compounds correspond to the formula $$R^1R^2R^3R^4N^+X^-$$

where
  $R^1$ to $R^4$—independently of one another—are C-1 to C-18-alkyl or benzyl and
  $X^-$ is iodide, chloride, hydroxide or hydrogen sulfate.

More preferred phase transfer catalysts are the tetrabutylammonium salts (i.e., wherein $R^1$ to $R^4$ are butyl).

Acids useful in the present invention with a pKa value which is less than or equal to 4 may be inorganic and organic acids. Acids with a pKa value of less than or equal to 1 are preferred. More Preference is given to inorganic acids. Most preference is given to HCl, HBr, sulfuric acid and nitric acid.

The amount of acid is 5 to 50% by weight, based on the amount of aqueous phase, preferably 10 to 30% by weight, based on the amount of aqueous phase.

Typically, the amount of paraldehyde, based on hydroxyacetone used, is 40 to 200% by weight, preferably 50 to 100% by weight.

Typically, the amount of paraldehyde in the metering mixture is 40 to 200% by weight, based on the amount of hydroxyacetone, preferably 50 to 100% by weight.

The metered addition of the metering mixture takes place at a reaction temperature (bottoms temperature) in the range from 35 to 100° C., preferably 40 to 75° C., more preferably 45 to 60° C. The temperature of the metering mixture is usually in the range from 0 to 40° C., preferably in the range from 10 to 30° C. The metering time is usually 1 to 30 hours, preferably 5 to 20 hours.

The process according to the present invention can be carried out in the presence of diluents. The addition of inert organic diluents is not required. A preferred diluent is water.

When the metered addition of the metering mixture is complete, a post reaction time may follow, preferably a post reaction time in the range from 0.05 to 3 hours, more preferably in the range from 0.1 to 1 hour.

Preferably, the completion of the metered addition is followed directly by distillation of the mixture containing water and 2,3-pentanedione. This distillation can be carried out under atmospheric pressure or under reduced pressure. In addition, this distillation can also be carried out with superheated steam, which is introduced into the reactor. The steam pressure is in the range from 3 to 10 bar.

Preference is given to a steam distillation at atmospheric pressure by the addition of water.

The chemical yield is typically around 85% of the starting material used in deficit, as a result of which an economic preparation of 2,3-pentanedione is possible.

According to the process of the present invention, it is possible to prepare 2,3-pentanedione with good reaction yield under gentle reaction conditions without the use of complex apparatuses from commercially available starting materials. The process according to the present invention is therefore suitable for the economic preparation of 2,3-pentanedione on a pilot-plant and industrial scale.

The process according to the present invention can, for example, be carried out as follows:

A metering mixture containing hydroxyacetone and paraldehyde and optionally a diluent is added dropwise to an aqueous solution containing an acid with a pKa value of less than or equal to 4 and a phase transfer catalyst. The reaction temperature is kept relatively constant, and is in the range from 35 to 100° C.

When the metered addition is complete, and optionally after a post reaction time, water is added, and a mixture which contains water and 2,3-pentanedione is distilled off from the reaction mixture. When distillation is complete, the

EXAMPLES

Example 1
Preparation of 2,3-pentanedione on a Laboratory Scale

Preparation of the metering mixture:

100 g of hydroxyacetone and 84 g of paraldehyde are mixed.

Carrying Out the Reaction:

27 g of concentrated hydrochloric acid, 33 g of water and 2.5 g of tetrabutylammonium bromide solution, 50% strength by weight in water, are combined and heated to 50° C. At this temperature, the metering mixture (temperature of metering mixture: 19–21° C.) is metered over the course of 7 hours.

A further 38 g of water are then added to the reaction mixture, and a mixture which contains water and 2,3-pentanedione is distilled off at atmospheric pressure. The phases are then separated, giving 125 g of 2,3-pentanedione, 92% strength by weight according to the gas chromatogram. This corresponds to a yield of 85% of the starting material used in deficit.

Example 2
Preparation of 2,3-pentanedione on a Pilot-Plant Scale

Preparation of the Metering Mixture:

150 kg of hydroxyacetone and 126 kg of paraldehyde are mixed.

Carrying Out the Reaction:

40 kg of concentrated hydrochloric acid, 50 kg of water and 4 kg of tetrabutylammonium bromide solution, 50% strength by weight in water, are introduced into the reactor one after the other and heated to 50° C. At this temperature the metering mixture (temperature of the metering mixture: 10° C.) is metered over the course of 10 hours.

A further 60 kg of water are then added to the reaction mixture, and a water/2,3-pentanedione mixture is distilled off at atmospheric pressure. The phases are then separated, giving 174 kg of 2,3-pentanedione, 94% strength by weight according to the gas chromatogram. This corresponds to a yield of 81% of the starting material used in deficit.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for the preparation of 2,3-pentanedione comprising reacting hydroxyacetone and paraldehyde in the presence of both an aqueous phase comprising a strong organic or inorganic acid with a pKa value of less than or equal to 4 and a phase transfer catalyst.

2. The process according to claim 1, wherein the phase transfer catalyst is a phosphonium, sulphonium or ammonium compound.

3. The process according to claim 1, wherein the amount of acid present is 5 to 50% by weight, based on the amount of aqueous phase.

4. The process according to claim 1, wherein the inorganic acid has a pKa value of less than or equal to 1.

5. The process according to claim 1, wherein the amount of paraldehyde is 40 to 200% by weight, based on the amount of hydroxyacetone.

6. The process according to claim 1, further comprising the step of adding a metering mixture comprising hydroxyacetone and paraldehyde and optionally a diluent, wherein the addition takes place at a reaction temperature from 35° C. to 100° C.

* * * * *